(12) United States Patent
Park et al.

(10) Patent No.: US 6,177,274 B1
(45) Date of Patent: Jan. 23, 2001

(54) HEPATOCYTE TARGETING POLYETHYLENE GLYCO-GRAFTED POLY-L-LYSINE POLYMERIC GENE CARRIER

(75) Inventors: Jong Sang Park; Young-Hun Choi, both of Seoul (KR); Feng Liu, Salt Lake City, UT (US)

(73) Assignee: Expression Genetics, Inc., Salt Lake City, UT (US)

(*) Notice: Under 35 U.S.C. 154(b), the term of this patent shall be extended for 0 days.

(21) Appl. No.: 09/315,240

(22) Filed: May 20, 1999

Related U.S. Application Data (60) Provisional application No. 60/086,072, filed on May 20, 1998.

(51) Int. Cl.$^7$ .......................... A01N 43/04; C07H 21/04; C12P 19/34
(52) U.S. Cl. ........................ 435/455; 514/44; 536/24.5
(58) Field of Search .................................. 435/325, 455, 435/91.31, 97, 91.1, 85, 375; 536/23.1, 25.6, 24.5, 25.3, 123.1, 123.13; 514/44; 530/396, 395, 300, 345, 350, 324, 383, 380, 402, 411, 421, 425

(56) References Cited

U.S. PATENT DOCUMENTS 5,733,762 * 3/1998 Midoux et al. ...................... 435/723
5,948,878 * 9/1999 Burgess et al. ...................... 528/272

FOREIGN PATENT DOCUMENTS

9621036 * 4/1996 (WO) ............................. C12N/15/87
9722371 * 6/1997 (WO) ............................. A61L/27/00

OTHER PUBLICATIONS

Branch, A. 1998 TIBS (Trends in Biotech Sci) vol. 23: 45–50.*
Crooke, S.T. 1998 Antisense Res & Appli. Chapt 1, pp. 1–50. Springer–Verlag—Berlin.*
Verma et al, 1997. Nature vol. 389: 239–242.*

* cited by examiner

Primary Examiner—George C. Elliott
Assistant Examiner—Jane Zara
(74) Attorney, Agent, or Firm—Thorpe North & Western LLP (57) ABSTRACT

A compound for targeted gene delivery is provided consisting of polyethylene glycol (PEG) grafted poly(L-lysine) (PLL) and a targeting moiety, wherein at least one free amino function of the PLL is substituted with the targeting moiety, and the grafted PLL contains at least 50% unsubstituted free amino function groups. TM is preferably lactose or galactose which are capable of specifically targeting a hepatoma cell or a liver cell. The new synthetic carriers with various substitution ratios of targeting moiety-PEG were characterized using NMR spectroscopy. The new polymeric gene carriers of this invention are capable of forming stable and soluble complexes with nucleic acids, which in turn are able to efficiently transform cells. PEG attached to the PLL gives better solubility properties to the gene/carrier complex and improved transfection efficiency without considerable cytotoxicity. Methods of preparing and using the targeting moiety-PEG-PLL as gene carriers to efficiently transfect cells are disclosed.

22 Claims, 8 Drawing Sheets

HEPATOCYTE TARGETING POLYETHYLENE GLYCO-GRAFTED POLY-L-LYSINE POLYMERIC GENE CARRIER

CROSS-REFERENCE TO RELATED APPLICATIONS

This application claims the benefit of U.S. Provisional Application No. 60/086,072, filed May 20, 1998.

BACKGROUND OF THE INVENTION

This invention relates to gene therapy. More particularly, the invention relates to a composition of polyethylene glycol-grafted poly-L-lysine and a hepatocyte cell targeting molecule-polyethylene glycol-grafted poly-L-lysine for gene delivery to a hepatocyte cell.

Twenty-five years ago Friedmann outlined prospects for human gene therapy. (T. Friedmann and R. Roblin (1972) Gene Therapy for Human Genetic Disease? 175 Science 949–955 (1972). Since then, gene therapy has represented a new paradigm for therapy of human disease and for drug delivery. The implicit emphasis of prior research has been on determining the safety of gene transfer procedures, often placing efficacy as a secondary goal. A major technical impediment to the gene transfer is the lack of an ideal gene delivery system. If it were possible to deliver the gene to the appropriate specific cells in sufficient quantities without adverse side effects, gene therapy would be efficacious. Currently very few organs or cells can be specifically targeted for gene delivery. There are many established protocols for transferring genes into cells, including calcium phosphate precipitation, electroporation, particle bombardment, liposomal delivery, viral-vector delivery, and receptor-mediated gene delivery. MS Wadhwa, Targeted Gene Delivery with a Low Molecular Weight Glycopeptide Carrier. 6 Bioconj. Chem. 283–291 (1995). Although all of these methods can be used for mammalian cultured cells, there are many difficulties in introducing genes into target cells in vivo.

Transfection methods using retroviral or adenoviral vectors overcome some of these limitations. Retroviral vectors, in particular, have been used successfully for introducing exogenous genes into the genomes of actively dividing cells such that stable transformants are obtained. D. G. Miller et al., Gene Transfer by Retrovirus Vectors Occurs Only in Cells that are Actively Replicating at the Time of Infection. 10 Mol. Cell Biol. 4239–4242 (1990). Viral vector systems often involve complementation of defective vectors by genes inserted into 'helper' cell lines to generate the transducing infectious agent. However, it is well known that the host immune response to adenoviruses limits their use as a transfer facilitating agent to a single administration. To address this limitation, fusion peptides of the influenza virus hemagglutinin have been employed to replace adenoviruses as endosomal lytic agents, but with limited success. S. Gottschalk et al. A Novel DNA-Peptide Complex for Efficient Gene Transfer and Expression in Manmmalian Cells, 3 Gene Ther. 448–457 (1996). However, despite their high transfection efficiency in vitro, inserting genes into the host cell's genome in this method depends on the viral infection pathway. The application of the viral infection pathway in application for human gene therapy introduces serious concerns about endogenous virus recombination, oncogenic effects, and inflammatory or immunologic reactions. G Ross et al., Gene Therapy in the United States: A Five-Year Status Report. 7 Hum. Gene Ther., 1781–1790 (1996). Because of these concerns, the use of viral vectors for human gene therapy has been extremely limited.

On the other hand, non-viral gene delivery systems such as cationic liposomes or synthetic gene carriers, e.g.poly-L-lysine (PLL), are being widely sought as alternatives. M. A. Wolfert et al., Characterization of Vectors for Gene Therapy Formed by Self-Assembly of DNA with Synthetic Block Co-Polymers. 7 Hum. Gene. Ther., 2123–2133 (1996); AV Kabanov & VA Kabanov DNA Complexes with Polycations for the Delivery of Genetic Materials into Cells. 6 Bioconj. Chem., 7–20 (1995). There are several advantages to the use of non-viral based gene therapies including their relative safety and low cost of manufacture. The major limitation of plasmid-based approaches has been that both the efficiency of gene delivery to several important somatic targets (i.e., liver and lung) and in vivo gene expression levels are lower using non-viral approaches than those using viral vectors.

Receptor-mediated gene delivery has its advantages and limitations. J. C. Perales et al., Biochemical and Functional Characterization of DNA Complexes Capable of Targeting Genes go [sic] Hepatocytes via the Asialoglycoprotein Receptor. 272 J. Biol. Chem.,7398–7407 (1997). Its advantages for use in gene therapy are as follows. First, the gene delivery carrier can be designed and customized for a specific target receptor. Second, the DNA does not have to integrate into the host cell genome to be expressed. Third, the delivery system is theoretically not limited by the size of the transgene. Finally, the technique does not involve the use of potentially infectious agents. There are also disadvantages that must be overcome before this procedure can be routinely used for human gene therapy. For example, the transgene is not integrated into the host cell chromosomes, or its expression is transient. Therefore, it will most likely be necessary to subject patients to multiple injections of a gene of interest. The DNA-ligand complexes are difficult to prepare and, until recently, little was known about their structure-function relationship. Also, there is only a fragmentary understanding of the biological process involved in the transfer of the transgene into the cell and its subsequent expression. These and other features of this system for gene therapy have recently been reviewed in detail. J. C. Perales et al., An Evaluation of Receptor-Mediated Gene Transfer Using Synthetic DNA-Ligand Complexes. 226 Eur. J. Biochem., 255–266 (1994).

In the mid 1970's, it was shown that PLL makes condensates with DNA. U. K. Laemmli Characterization of DNA Condensates Induces by Poly(ethylene oxide) and Polyl-ysine. 72 Proc. Nat'l. Acad. Sci. U.S.A., 4288–4292 (1975). Since then, PLL modified with various substances, has been used as a gene carrier. (M. S. Wadhwa et al., Targeted Gene Delivery with a Low Molecular Weight Glycopeptide Carrier. 6 Bioconj. Chem., 283–291 (1995); A. Maruyama et al., (1997) Nanoparticle DNA Carrier with Poly(L-lysine) Grafter Polysaccharide Copolymer and Poly(D,L-lactic acid). 8 Bioconj. Chem., 735–742; G. Y. Wu, and C. H. Wu, Evidence for Targeted Gene Delivery to Hep G2 Hepatoma Cells in vitro., 27 Biochemistry, 887–892 (1988); P. Midoux et al., Specific Gene Transfer Mediated by Lactosylated Poly-L-Lysine into Hepatoma Cells. 21 Nucleic Acids Res., 871–878 (1993); P. Erbacher et al., Glycosylated Polylysine/ DNA Complexes: Gene Transfer Efficiency in Relation with the Size and the Sugar Substitution Level of Glycosylated Polylysines and with the Plasmid Size. 6 Bioconj. Chem., 401–410 (1995).

PLL itself can be used as a DNA condensate. U.K. Laemmli, Characterization of DNA Condensates Induces by Poly(ethylene oxide) and Polylysine. 72 Proc. Nat'l. Acad.

Sci. U.S.A. 72, 4288–4292 (1975)). However, the use of PLL alone as a gene delivery carrier has several disadvantages. First, its transfection efficiency is very low, because PLL has no functional group except the amine group used in charge-neutralization. Also, due to the negative charges of the DNA phosphate backbone, an increase in the degree of charge neutralization of the DNA often results in extensive condensation and the separation of the DNA phase in the form of insoluble compact structures. J. C. Perales et al., Biochemical and Functional Characterization of DNA Complexes Capable of Targeting Genes go [sic] Hepatocytes via the Asialoglycoprotein Receptor. J. Biol. Chem. 272, 7398–7407 (1997); D. E. Olins et al., Model Nucleoprotein Complexes: Studies on the Interaction of Cationic Homopolypeptides with DNA. 24 J. Mol. Biol., 157–176 (1967); J. T. Shapiro et al., Deoxyribonucleic Acid-Polylysine Complexes. Structure and Nucleotide Specificity. 8 Biochemistry 3219–3232 (1969).

In view of the foregoing, it will be appreciated that providing a targeted composition of gene therapy and a method for using thereof would be of a significant advancement in the art.

BRIEF SUMMARY OF THE INVENTION

It is an object of the present invention to provide a composition that efficiently mediates DNA delivery into a targeted cell.

It is a further object of the present invention to provide a biocompatible composition for efficient DNA delivery causes the non-cytotoxic transfection into a targeted cell.

It is an additional object of this invention to provide a method for delivering DNA into a targeted cell.

These and other objects are accomplished through the synthesis of a composition that contains a polylysine member covalently grafted to a certain percentage of polyethylene glycol members, which are in turn covalently bound to a targeting moiety. Furthermore, this composition mediates transfection of DNA or gene moieties into human cells. This transfection method and composition accomplish these goals while presenting minimum cell toxicity and significantly increased transfection efficiency.

Accordingly, polymers for addressing these objects were synthesized by coupling a targeting moiety(TM) to an end of a PEG polymer and covalently attaching the other end of TM-PEG to the ε-amino group of PLL. The targeting moiety is preferably a lactose or a galactose. The purpose of using the targeting moiety is to target cells for gene delivery to the particular cells. The ratio of TM-PEG and PLL can be adjusted by changing reaction conditions. The synthesized carrier, namely TM-PEG-PLL, wherein 5–30% of amino groups on PLL being conjugated with TM-PEG with the rest of the amino groups remaining as unsubstituted free amino groups, is capable of forming a stable and soluble complex with a nucleic acid, which in turn is capable of efficient transfection. The PEG moiety grafted to PLL resulted in better solubility and reduced cytotoxicity of the nucleic acid/carrier complex as compared to PLL alone. Compared with PLL without PEG as disclosed in U.S. Pat. No. 5,733,762, the PEG grafted PLL of this invention provides a high solubility of the complexes formed with DNA in physiological serum and cell culture medium, and prevents the precipitation and aggregation of the complexes (or nanopaticles) formed, and thus is capable of being administrated in vivo at very high dosage levels. The gene transfection efficiency and cytotoxicity of the TM-PEG-PLL system were investigated and compared to those of DNA complexed with PLL alone. Hep G2 cells, as an example, were transfected specifically with a plasmid DNA/Lac-PEG-PLL complex, indicating that lactose serves as a targeting moiety for hepatoma cell line. The PEG-PLL of this invention also decreases the proteolytic degradation of DNA in circulatory system and in cells, and enhances the fusing of cell membranes, thus improves transfection efficiency. In addition, PEG also functions as a linker connecting the PLL backbone and the targeting moiety, thus increasing the targeting efficiency of DNA delivery to the targeted cells.

DETAILED DESCRIPTION OF THE INVENTION

Before the present composition and method for gene delivery are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof. It must be noted that, as used in this specification and the appended claims, the singular forms "a," "an," and "the" include plural referents unless the context clearly dictates otherwise.

This invention relates to a composition capable of forming stable, soluble complexes with nucleic acids and the method of preparation thereof comprising a polylysine (PLL) member covalently bound to a polyethylene glycol member (PEG-PLL), which in turn covalently bound to a a targeting moiety(TM), recognizable by cell membrane receptors. The complexes are able, upon dissociation to release the nucleic acid to transfect several types of cells and the targeting moiety(TM) makes the transfection selective to cells containing the receptors of the TM. This invention also provides a method for specific cell transfection in vitro or in vivo. The TM is preferably a lactose or a galactose which is selectively targeting a hepatoma cell.

The invention, in one of its most general definitions, concerns a complex between at least one negatively charged nucleic acid and at least one positively charged polymeric conjugate, the association between the nucleic acid and the polymeric conjugate being electrostatic in nature, said positively charged polymeric conjugate consisting essentially of poly-L-lysine(PLL) and PEG, wherein about 5 to 30% of $NH_3^+$ of the PLL(20–30K MW) is covalently linked to PEG(0.5–20K MW), which in turn also covalently linked to a targeting moiety(TM). The PEG-PLL gene carrier of this invention allows a condensation of the DNA which remains very strong as a result of a cooperative phenomenon between the positive charges of the PLL and the negative charges of the nucleic acid. In addition, the addition of PEG on part of the amino groups of the PLL prevents the precipitation and aggregation of the complexes (or nanoparticles) formed by PEG-PLL and nucleic acid, thus increasing the solubility of the complexes. The PEG linked to PLL also functions to fuse the cell membranes and prevents the proteolytic degradation of nucleic acid, thus increasing the transfection efficiency. Furthermore, since PEG can serves as a linker connecting PLL backbone and the targeting moiety(TM), it increasing the targeting efficiency of the complexes.

In the composition of this invention, the targeting moiety (TM) could be any signal member which is recognizable by a cell membrane receptor, preferably, TM is a galtactose containing saccharide which specifically binds liver cells or hepatoma cells. Preferably, the galactose containing sacchride is a member selected from the group consisting of lactose and galactose.

The composition of the invention can form stable and soluble complexes with nucleic acids which can effectively transfect mammal cells. The nucleic acid can be chosen among the following items: a) gene markers, such as luciferase gene, β-galactosidase gene, chloramphenicol acetyl transferase gene, genes bestowing the resistance to an antibiotic, such as hygromycin or neomycin; b) genes for therapeutic purposes, such as the gene encoding low density lipoprotein receptors, deficient in the case of hypercholesterolemia (liver), coagulation factors, gene suppressers of tumors, major histocompatibility proteins, antioncogenes, sense and antisense RNA, and ribozymes; and c) genes with vaccine purposes, such as genes encoding viral antigens.

PEG employed in the present invention has MW from 0.5 to 20 K, preferably, 0.5 to 5K Dalton with repeating units from 11 to 114.

PLL employed in the present invention has MW from 2 to 100 K, preferably, 15 to 50K with repeating units from 10 to 250.

The plasmid carrying a gene to be delivered was delivered into targeted liver cells using the composition of the present invention with enhanced transfection efficiency, compared to that of PLL alone. Plasmid pSV-β-gal, which is a modification of pRSV-β-galactosidase vector, is often used as a marker gene for monitoring gene expression in mammalian cells. Promega Co. pSV-β-galactosidase Control Vector Map and Sequence. TB094 Promega Technical Bulletin 1 (1994). The SV40 early promoter and enhancer drive the transcription of the lacZ gene in mammalian cells. β-galactosidase is an excellent reporter enzyme. N Rosenthal, (1987) Identification of Regulatory Elements of Cloned Genes with Functional Assays. 152 Methl. 704–720 (1987), and can be assayed quickly and directly in cell extracts using a spectrophotometric assay.

Figure 3:
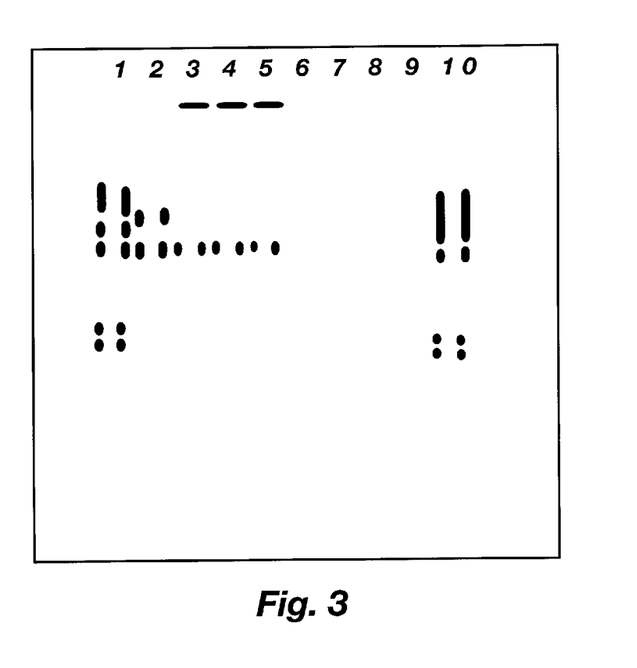
FIG. 3 shows an illustrative band retardation assay using 30 mole % Lac-PEG-PLL. Lane 1 and 10: Molecular weight marker; Lane 2: plasmid DNA(1 μg); Lane 3: plasmid DNA(1 μg)+Lac-PEG-PLL(1 μg); Lane 4: plasmid DNA (1 μg)+Lac-PEG-PLL(0.3 μg); Lane 5: plasmid DNA(1 μg)+Lac-PEG-PLL(0.5 μg); Lane 6: plasmid DNA(1 μg)+Lac-PEG-PLL(1 μg); Lane 7: plasmid DNA(1 μg)+Lac-PEG-PLL(3.0 μg); Lane 8: plasmid DNA(1 μg)+Lac-PEG-PLL (5.0 μg); Lane 9: plasmid DNA (1 μg)+Lac-PEG-PLL(10.0 μg).

It was shown that lactose-PEG-modified PLL has the ability to form complexes with pSV-β-gal from band retardation assay (FIG. 3). The shift of the pSV-β-gal/Lac-PEG-PLL band during electrophoresis depends on the pSV-β-gal:Lac-PEG-PLL ratio that alters the complex net charge as well as its size and density. A. V. Kabanov & V A Kabanov, DNA Complexes with Polycations for the Delivery of Genetic Materials into Cells. 6 Bioconj. Chem., 7–20 (1995). The decrease in the electrophoretic mobility of pSV-β-gal/Lac-PEG-PLL complex was accompanied by an increase in the content of Lac-PEG-PLL in the system, and it is due to neutralization of the DNA negative charge by the carrier positive charge. Formation of a DNA-carrier complex was also observed in a dye displacement assay.

A method of in vitro or in vivo transfection of the present invention includes the introduction of a complex of nucleic acids and a PEG grafted PLL polymeric carrier into a medium containing cells to be transfected under conditions such that there exists: passage of the complex from the medium into the cytoplasm of the cells, release of the nucleic acid of the aforementioned complex into the cytosol of the cells, transcription and expression of the nucleic acid in the transfected cells.

As discussed earlier, one of the problems of unmodified PLL as a gene carrier is that complexation between PLL and DNA frequently results in formation of fine precipitates, limiting the concentration that can be used. T. D. McKee et al., Preparation of Asialoorosomucoid-polylysine Conjugates. 5 Bioconj. Chem., 306–311 (1994). Accordingly, complexation of pSV-β-gal with PLL in 20 mM HEPES (pH 7.4) with 0.15 M NaCl resulted in precipitates at 50 μg/mL of pSV-β-gal. Whereas the, PEG-g-PLL and TM-PEG-PLL of the present invention maintained the solubility of pSV-β-gal when they made complexes with DNA at this concentration. Therefore, it is apparent that the attached PEG moiety makes pSV-β-gal/gene carrier complexes substantially more soluble and thereby more functional.

The invention also refers to a process of preparation of the composition of PEG grafted PLL as a polymeric gene carrier described above. As examples, the process for synthesizing Lac-PEG-PLL and Gal-PEG-PLL are described in the FIGs and Examples 1, 15, and 16.

The invention also refers to the use of a complex formed by nucleic acid and the polymeric gene carrier according to the invention for the transfection of cells which may be chosen from the following: cells from hematopoietic strains; liver cells; cells of skeletal muscles; skin cells such as fibroblasts, keratinocytes, dendritic cells, or melanocytes;

cells of the vascular walls such as endothelial cells or smooth muscle cells; epithelial cells of the respiratory tract; cells of the central nervous system; cancer cells; cells of the immune system, such as lymophocytes, macrophages, NK cells, etc.

The gene delivery ability of the synthesized carriers Lac-PEG-PLL as an example of the present invention and its specificity were investigated. Hep G2 cells were chosen for the specificity test because they have specific lactose receptors on their surface. The recognition of lactose is mediated by the lactose receptors on liver cells. L. Stryer, Carbohydrates. Biochemistry (3rd ed.) P. 345, WH Freeman and Company, New York (1988). They are used for removal of glycoproteins from the blood. Many newly synthesized glycoproteins, such as immunoglobulin and peptide hormones, contain carbohydrate units with terminal sialic acid and galactose residues. During hours or days, depending on the particular protein, terminal sialic acid residues are removed by sialylases on the surface of blood vessels. The exposed galactose residues of these trimmed proteins are detected by the asialoglycoprotein receptors in the plasma membranes of liver cells. The complex of the asialoglycoprotein and its receptor is then internalized into the liver cell, by an endocytosis process, to remove the trimmed glycoprotein from the blood. The present disclosure shows that the lactose moiety on the carrier can serve as a targeting material for the hepatoma cell line.

Figure 1:
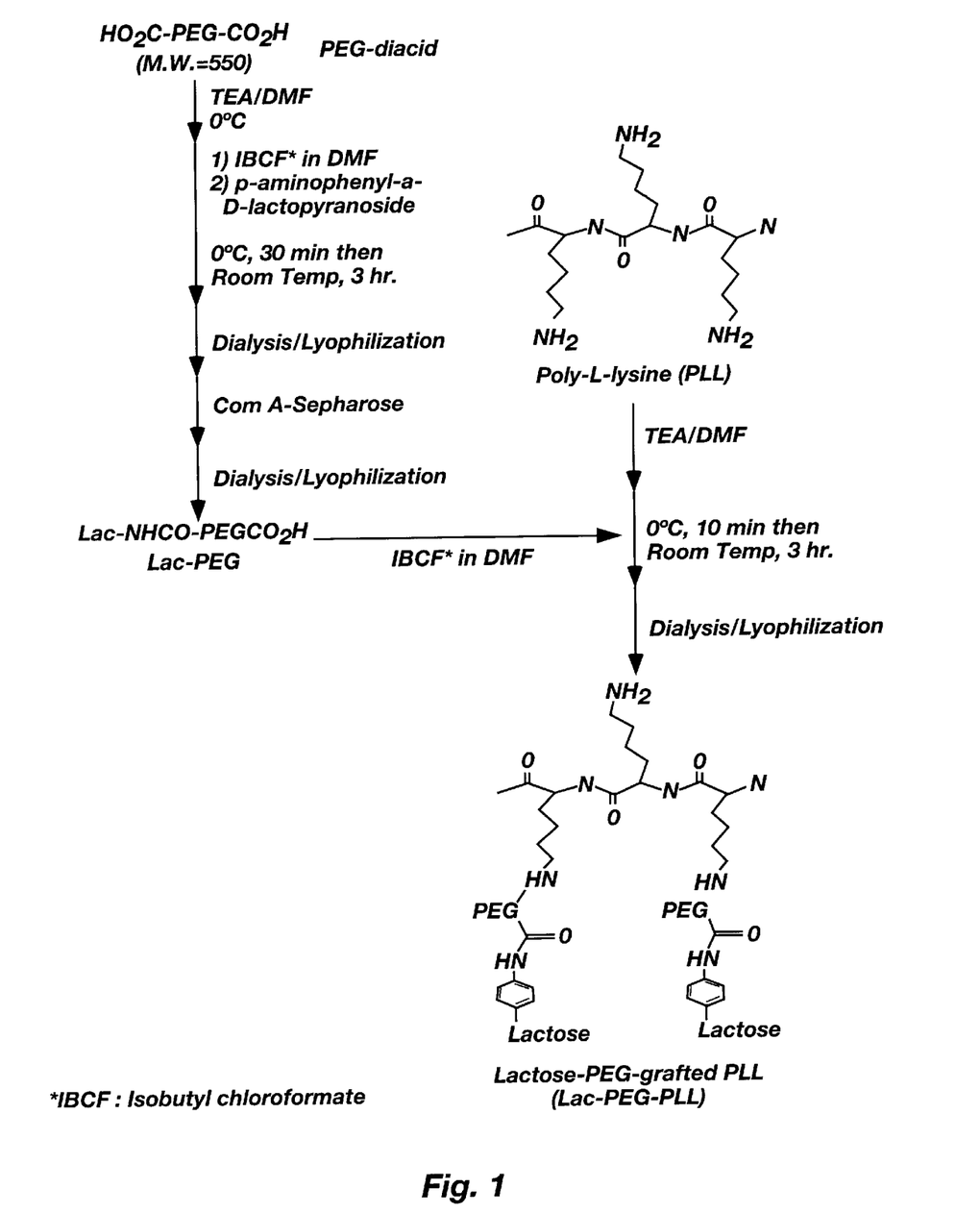
FIG. 1 shows the scheme for synthesis of Lac-PEG-PLL.

Lac-PEG-PLL was synthesized by a scheme comprising two reactions, synthesis of lactose-PEG diacid and synthesis of the comb-shaped polymer Lac-PEG-PLL from lactose-PEG diacid and PLL (FIG. 1 and FIG. 15). In the first reaction, isobutyl chloroformate (IBCF) and a carboxylic acid in the PEG diacid formed an active ester, and a molecule of hydrochloric acid was released. Triethanolamine (TEA) was used as a base to neutralize the hydrochloric acid that was formed during the reaction. The amino group in p-aminophenyl-α-D-lactopyranoside reacted with the ketone group on PEG, forming an amide bond between the sugar and PEG. After a 4-hour reaction, the products were precipitated using an excess of ethyl ether. The precipitates were then re-dissolved in distilled water and dialyzed using a dialysis membrane, 1,000 MWCO, to remove unreacted p-aminophenyl-α-D-lactopyranoside. A Con A-Sepharose column was used to remove unreacted PEG. Lactose-PEG diacid was dissociated from the Con A-Sepharose column through the application of 0.1 M methyl-α-D-mannopyranoside-containing buffer to the composition. The lactose-PEG-lactose fraction where both carboxylic acid sides of the PEG diacid had been esterified with a lactose moiety was eluted with lactose-PEG diacid, but no further purification was required, because lactose-PEG-lactose is not reactive under the second reaction conditions. Also the lactose-PEG-lactose was removed completely during the dialysis in the second reaction. In the second reaction, IBCF activated the carboxylic acid in lactose-PEG, facilitating the formation of amide bond between the amino group on PLL and a carboxylic acid or ester.

The Lac-PEG-PLL polymers of this invention make a complex with pSV-β-gal. The Lac-PEG-PLL compound of this invention makes the complex soluble, while the complex between pSV-β-gal and PLL alone formed a fine precipitate. The Lac-PEG-PLL carrier/DNA complex has more than 10-fold increase in transfection efficiency when compared to that of a PLL complex on Hep G2 cells. This increase may be due to the cell targeting effect of lactose moiety, and partially from the fusogenic effect of PEG. The attached PEG group also allows the Lac-PEG-PLL and the pSV-β-gal/Lac-PEG-PLL complex to be less cytotoxic than PLL. The lactose moiety specifically serves as a targeting moiety for the transfection into hepatocyte cells. This was demonstrated by two pieces of evidence. First, free lactose inhibited transfection at millimolar concentrations. Second, very low transfection efficiency was monitored when other lactose receptor-deficient cell lines were used for transfection. The existence of FBS and chloroquine improved transfection, further demonstrating that transfection occurred via an endocytosis mechanism.

The following Examples are presented to illustrate the process of preparing the composition and method of using the composition of the present invention.

EXAMPLE 1
Synthesis of Lac-PEG Diacid

The synthesis of lactose-PEG diacid was carried out as follows. Six hundreds milligrams (1.0 mM) of PEG diacid (mol. wt.=600; Fluka, Ronkonkoma, N.Y.) was dissolved in 1.5 mL of dried N, N-dimethyl formamide (DMF; Aldrich) containing 1.0 mM of triethylamine (TEA; Aldrich) in an ice-water bath under nitrogen. One mM of isobutyl chloroformate (IBCF; Aldrich) dissolved in 1.0 mL of dried DMF was added dropwise, and the mixture was stirred for 15 min in an ice-water bath. IBCF served as the activator of carboxylic acid. Then p-aminophenyl-α-D-lactopyranoside (1.0 mM; Sigma) dissolved in 1.0 mL of DMF was added, and the mixture was stirred 30 min in an ice-water bath and then for an additional 3 hours at room temperature. The product was precipitated in an excess of dry ether (25 mL). Then the precipitate was dissolved in 20 mL of distilled water, dialyzed against distilled water (dialysis tubing with MWCO 1,000; Spectrum, Houston, Tex.), and freeze-dried. The product was purified by removing unreacted PEG diacid on a Con A-Sepharose column (Sigma). Forty milligrams of the lyophilized product was dissolved in 40 mL of 0.02 M Tris buffer (pH 7.4), 0.5 M NaCl, 3 mM CaCl2 and 3 mM MnCl2 and loaded on Con A-Sepharose column at a flow rate of 0.10 mL/min. The column was eluted until absorbance at 280 nm dropped below 0.01, and then a similar buffer but containing 0.1 M methyl-α-D-mannopyranoside (Sigma) was applied. The specifically eluted peak of lactose-PEG and lactose-PEG-lactose mixture was detected by monitoring at 280 nm, collected, dialyzed against distilled water, and finally freeze-dried. The content of carboxylic acid was assayed by titration. The mole ratio of lactose-PEG to lactose-PEG-lactose was about 2:1.

EXAMPLE 2
Grafting of Lactose-PEG Diacid to PLL

In this example, the synthesis of lac-PEG-PLL with 30% (mole/mole %) lactose-PEG is described. Lactose-PEG and lactose-PEG-lactose mixture (51.5 mg; containing 0.042 m of lactose-PEG) prepared according to the procedure of Example 1 was dissolved in 0.5 mL of dried DMF under nitrogen in an ice-water bath. IBCF (0.036 m) dissolved in 0.5 mL of DMF was added to the above solution dropwise. The mixture was stirred 30 min in an ice-water bath and then added dropwise to 1 mL of dried dimethylsulfoxide(DMSO; Aldrich) containing 25 mg of PLL-HBr (120 repeating units; mol.wt.=25,000; Sigma) and 10 µL of TEA, which had been purged with nitrogen for 10 min in an ice-water bath, then stirred additional 3 hours at room temperature. The product was precipitated in 100 mL of dried ether, and the precipitate was dissolved in 10 mL of distilled water. It was dialyzed (dialysis tubing with MWCO 25,000) against a 0.01 M NaHCO3 solution, then against a 0.01 M HCl solution, and then against distilled water. The dialyzed product was finally freeze-dried. The mole ratios of lactose-PEG to the amine group in PLL were calculated from 1H-NMR.

EXAMPLE 3
1H-NMR Analysis of Lactose-PEG-PLL

Figure 2:
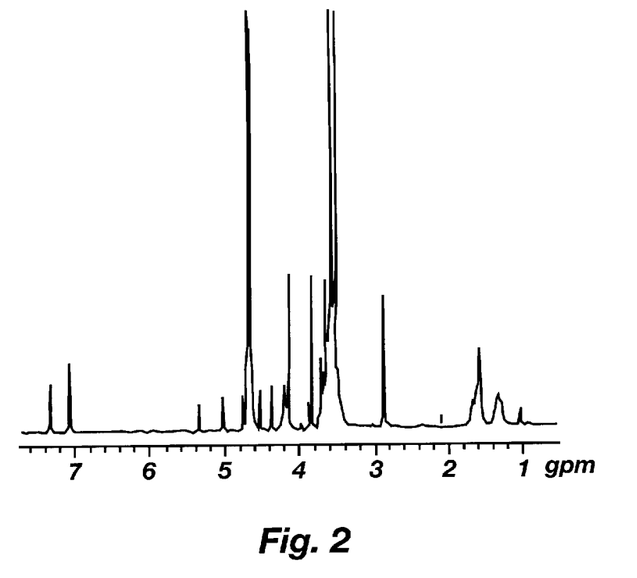
FIG. 2 is a depiction of an illustrative 1H-NMR analysis of Lac-PEG-PLL wherein the peak at about 3.5 ppm designates the existence of PEG in the composition.

1H-NMR analysis of Lac-PEG-PLL, prepared according to the procedure of Example 1 and 2 was carried out in H2O. The 1H-NMR spectrum of 30 mole % Lac-PEG-PLL is shown in FIG. 2. The peak at about 3.5 ppm is indicative of the presence of PEG in the compositions. The content of PEG was calculated from the NMR spectrum by relating the PEG (—CH2CH2—.s.3.4–3.7 ppm) peak and side chain of PLL (—CH2CH2 CH2—.m.1.1–1.8 ppm) peak. From this method the lactose-PEG content ratios of four illustrative carrier composition prepared according to the present invention were verified as follows: 6, 12, 20, and 30 mole %, respectively.

EXAMPLE 4
Physicochemical Characterization: Band Retardation Assay

Experiments were performed to investigate whether the Lac-PEG-PLL composition according to the present invention formed complexes with pSV-β-gal plasmid DNA (Promega Corp., Madison, Wis.; EMBL accession No. X65335). Various amounts of Lac-PEG-PLL prepared according to the procedure of Example 1 and 2, ranging from 0.1 to 10 μg, were added to 1 μg of plasmid DNA and incubated for 30 min at room temperature. Gel electrophoresis sample buffer was added to each sample, and the samples were then fractionated by electrophoresis on 1% (w/v) agarose gel for 90 min at 100 V using the Easy-Cast™ Electrophoresis System (Owl Scientific Inc., Woburn, Me.). TBE (45 mM Tris-Borate, 1 mM EDTA, pH 8.0) buffer was used as electrophoresis buffer. The gel was stained with ethidium bromide (0.5 μg/mL) for 30 min and illuminated with an UV illuminator to show the location of the DNA. Lambda DNA (Promega), which was digested by Eco RI, was used as a DNA size marker.

EXAMPLE 5
Physicochemical Characterization: Solubility

The solubility of the carrier/plasmid DNA complex was determined by a method developed by Wadhwa et al. (MS Wadhwa et al., Targeted Gene Delivery with a Low Molecular Weight Glycopeptide Carrier. 6 Bioconj. Chem., 283–291(1995), with a slight modification. pSV-β-gal plasmid DNA and Lact-PEG-PLL carrier, prepared according to the procedure of Example 1 and 2, were mixed in 1 mL of a buffer containing 20 mM HEPES, 0.15 M NaCl, pH 7.4, with a final concentration of 50 μg/mL in 1.5 mL centrifuge tubes. After incubation for 30 min at room temperature, the tubes were centrifuged for 5 min at 10,000 rpm. The supernatant was taken and its absorbance at 260 nm was measured for the determination of the DNA remaining in solution. A DNA sample without carrier was used as a standard. Comparative complexes were formed by mixing DNA with either PLL or PEG-g-PLL (prepared according to U.S. Ser. No. 60/069,351, hereby incorporated by reference).

Figure 4:
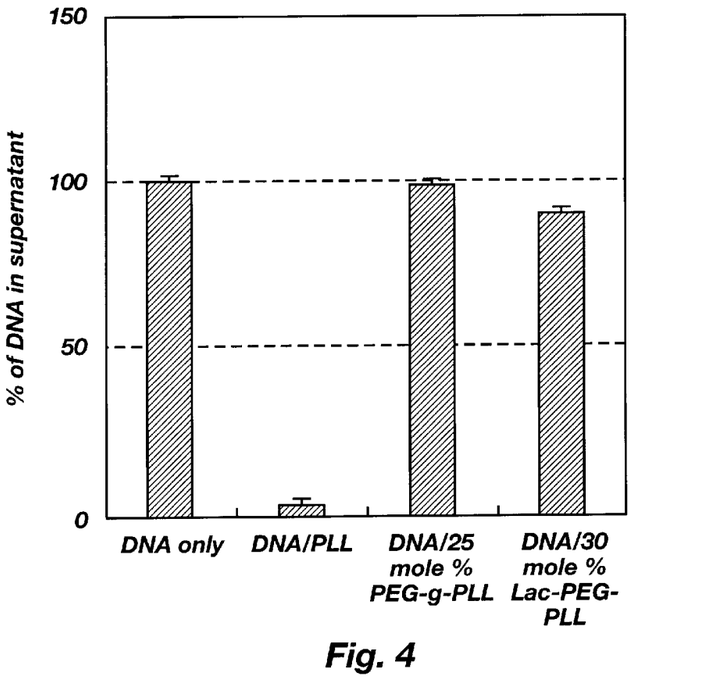
FIG. 4 shows the results of a test of the solubility of Plasmid pSV-β-gal and in Lac-PEG-PLL.

Plasmid DNA/carrier complexes were defined as soluble if centrifugation under the conditions selected failed to remove DNA from the supernatant. FIG. 4 shows that formation of complexes between pSV-β-gal and PLL at a final concentration of 50 μg/mL led to the formation of a fine precipitates, which sedimented upon centrifugation at 10,000 rpm for 5 min. However, when the PEG-modified PLL was used to make complex with pSV-β-gal, nearly 98% of the DNA remained in the supernatant after centrifugation. The modification of the end of the PEG group with a lactose moiety did not give more than a 10% of decrease of solubility when compared to that of pSV-β-gal/PEG-g-PLL complexes. Thus, the attached PEG groups on PLL prevent the pSV-β-gal/carrier complexes from making fine precipitates and becoming insoluble.

EXAMPLE 6
Transfection

The in vitro transfection efficiency of Lac-PEG-PLL synthesized according to example 1 and 2 was evaluated using the Hep G2 cell line (ATCC No. HB 8065). Hep G2 cells, a human hepatoma (liver carcinoma) cell line, which has a specific lactose receptor on its surface. The cells were maintained in MEM medium supplemented with 1 mM sodium pyruvate and 10% FBS (Hyclone, Logan, Utah) at 37° C. in a 5% CO2 Napco™ incubator (Precision Scientific Inc., Chicago, Ill.). For transfection experiments, various pSV-β-gal/PEG-g-PLL complexes were formulated with a fixed amount of pSV-β-gal (10 μg/mL) and increasing amounts of Lac-PEG-PLL (1–100 μg/mL). The cell culture media without FBS was used as a mixing medium.

In vitro transfection in general was performed as follows. Hep G2 cells were seeded at a density of 20×104 cells/mL, 100 μL/well, in 96-well flat-bottomed microassay plates (Falcon Co., Becton Dickenson, Franklin Lakes, N.J.), and incubated for 24 h before the addition of either the plasmid DNA/carrier complex or the carrier only.

The Lac-PEG-PLL carriers were sonicated for 6–8 min using a probe type sonicator (Sonifer 250, branson) prior to transfection. All reagents used in the transfection experiments were sterilized by filtering through 0.22 μm polycarbonate membrane filters. Plasmid pSV-β-gal/Lac-PEG-PLL complexes were prepared by mixing 1 μg of pSV-β-gal and various amounts of carrier in 100 μl FBS-free cell culture medium, and incubated for 30 min at room temperature. FBS and chloroquine were added at a final concentration of 10% (v/v) and 100 μM, respectively. Medium from each well of the 96-well plate was replaced with 100 μL of transfection mixture. The cells were then incubated for 4 h at 37° C. in a 5% CO2 incubator. After 4 h, the transfection mixtures were removed and 100 μL of fresh medium containing 10% FBS was added to each well. Cells were incubated for an additional 48 h at 37° C. Transfection efficiency was assayed by measuring β-galactosidase activity introduced into the cells by pSV-β-gal. The β-galactosidase activity in transfected cells was determined spectrophotometrically at 420 nm using O-nitrophenyl-b-D-galactopyranoside (ONPG; Sigma) with a slight modification. J. R. Saneset al., Use of a Recombinant Retrovirus to Study Post-Implantation Cell Lineage in Mouse Embryos. 5 EMBO J., 3133–3142 (1986), hereby incorporated be reference. The growth medium was removed from the cells in the 96-well plates to be assayed, and the cells were carefully washed twice with 1X PBS to prevent adherent cell detachment. Cells were lysed by adding 60 μL of 1X reporter lysis buffer (Promega, Madison, Wis.) to the cells and incubating for 30 min at room temperature, rocking the plate halfway through the incubation period, followed by scraping the cells. Sixty microliters of ONPG (1.33 mg/mL) in 2X assay buffer (Promega, Madison, Wis.) was added to the lysed cells and the cells were incubated at 37° C. for 4 h. The reaction was terminated by adding 150 μL of 1 M sodium carbonate solution to each well and the absorbance at 420 nm was read with a Bio-Tek EL-311 microplate reader (Bio-Tek Instrument Co., Winooski, Vt.) for the β-galactosidase activity.

The transfection efficiency of the synthesized Lac-PEG-PLL was evaluated using in vitro Hep G2 cell line. Hep G2 cell, a hepatoma cell line, has a specific lactose receptor on its surface. For the transfection experiments, various pSV-β-gal/Lac-PEG-PLL complexes were formulated with a fixed amount of pSV-β-gal (10 μg/mL) and increasing amounts of Lac-PEG-PLL (1–100 μg/mL). The cell culture media without FBS was used as a mixing medium.

Figure 5:
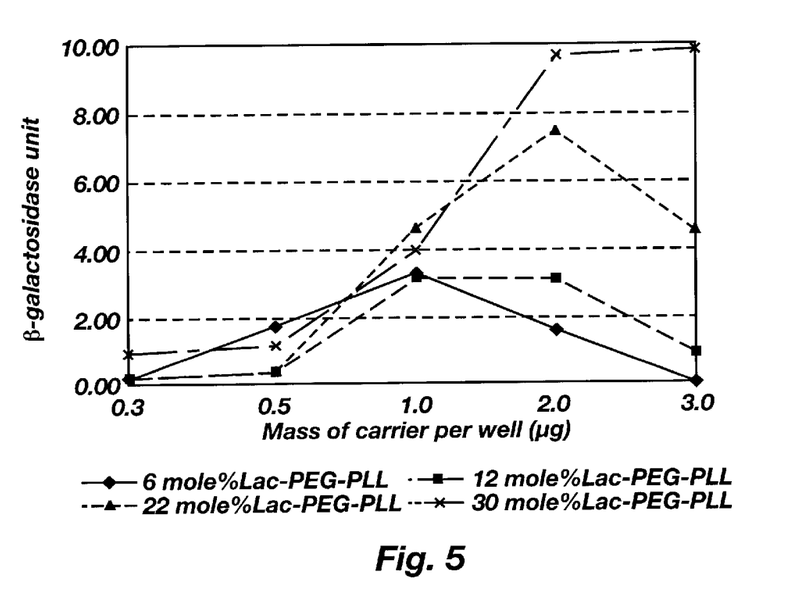
FIG. 5 is a graphical representation showing results of transfection experiments using different degrees of lactose-PEG substitution. ( ) 6 mol % Lac-PEG; ( ) 12 mole % Lac-PEG-PLL; ( ) 22 mole % Lac-PEG-PLL; ( ) 30 mole % Lac-PEG-PLL.

The Lac-PEG-PLL showed transfection ability into Hep G2 cells (FIG. 5). Below a 1:1 weight ratio of pSV-β-gal/Lac-PEG-PLL (0.3 or 0.5 mg carrier) very weak or no transfection efficiency was observed regardless of using any lactosylated carrier. At 1:2 and 1:3 weight DNA/carrier ratios, those carriers with higher lactose quantity showed higher efficiency. The 30 mole % Lac-PEG-PLL was the best carrier among the 4 lactosylated carriers both of these ratios. Although this invention is not limited to any proposed scientific explanation, this enhanced efficiency may be due to the targeting ability of lactose to Hep G2 cells, which reveals a rather different tendency from the case of PEG-g-PLL. As previously discussed, 10 mole % PEG-g-PLL showed a higher efficiency than 25 mole % PEG-g-PLL. Using 30 mole % Lac-PEG-PLL carrier, the highest transfection efficiency was achieved at 1:3 weight ratio, but the 1:2 weight ratio revealed transfection of almost the same magnitude. It was shown that the higher the lactose-PEG substitution degree in the carrier, the greater the quantity of carrier required to reach the highest transfection efficiency. When 5 mole % Lac-PEG-PLL was used, a 1:1 ratio complex showed the highest efficiency. In the case of 30 mole % Lac-PEG-PLL, the 1:3 ratio complex showed the highest efficiency. This may be explained by the ability of the gene carrier to make complexes with pSV-β-gal. Higher substituted Lac-PEG-PLL has less free amine to interact with negative charges on DNA. Therefore, more carrier is needed to make a complex with DNA to the same extent as a Lac-PEG-PLL containing a lesser amount of free amine interactions.

Figure 6:
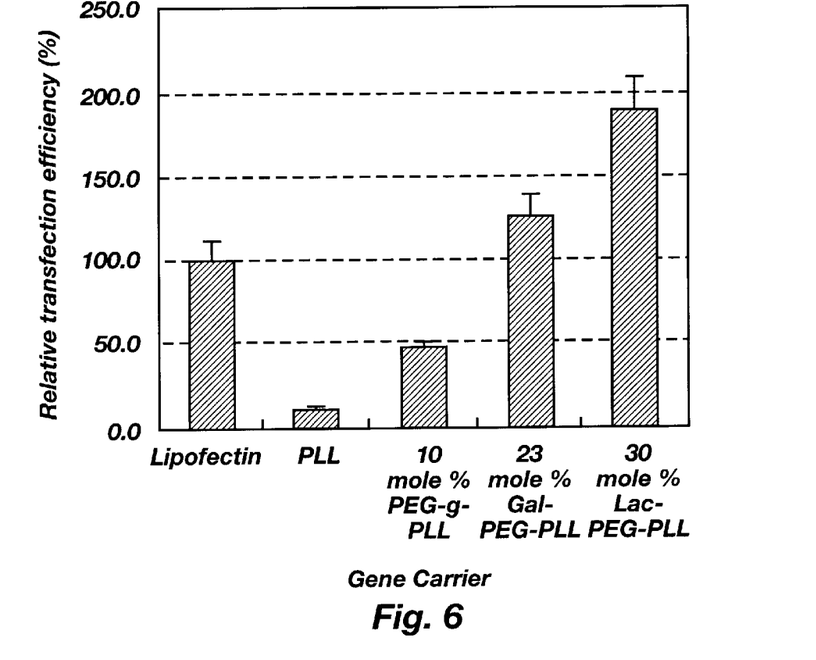
FIG. 6 shows a comparison of transfection efficiencies of LIPOFECTIN, PLL, PEG-g-PLL, Gal-PEG-PLL, and Lac-PEG-PLL as polymeric gene carriers in Hep G2 cells.

FIG. 6 summarizes the results for the transfection using PLL and modified PLL. LIPOFECTIN reagent (GIBCO/BRL, Gaithersburg, Md.) was used for the comparison of transfection efficiency. Among the carriers used in this experiment, PLL, PEG-g-PLL, and Lac-PEG-PLL—and LIPOFECTIN, Lac-PEG-PLL showed the best efficiency for Hep G2 cells.

Lac-PEG-PLL showed improved transfection efficiency over PLL and PEG-g-PLL. Among Lac-PEG-PLLs with different modified rations, 30 mole % Lac-PEG-PLL accomplished the highest efficiency at a 1:3 weight ratio to pSV-β-gal. It demonstrates that the lactose moiety on the end of PEG renders cell targeting ability to pSV-β-gal/Lac-PEG-PLL complexes. Furthermore, the fusogenic ability of PEG may serve as another factor for the increase of transfection efficiency observed. This assertion is supported by the fact that PEG is known to associate with the phospholipid head group of cell membranes, assisting modified proteins to penetrate into cell membranes. M. Yamazaki & T. Ito, Deformation and Instability in Membrane Structure of Phospholipid Vesicles Caused by Osmophobic Association: Mechanical Stress Model for the Mechanism of Poly (ethylene glycol)-induced fusion. 29 Biochemistry, 1309–1314 (1990).

EXAMPLE 7
Cytotoxicity

Figure 7:
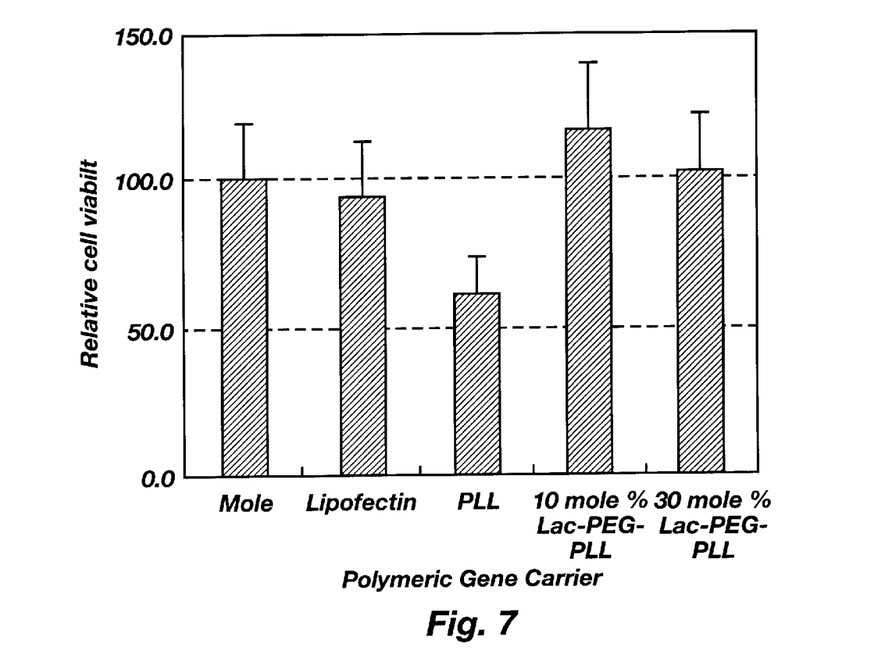
FIG. 7 shows a comparison of cytotoxicity of control medium, LIPOFECTIN, PLL, PEG-g-PLL, Gal-PEG-PLL, and Lac-PEG-PLL as polymeric gene carriers in Hep G2 cells.
Figure 8:
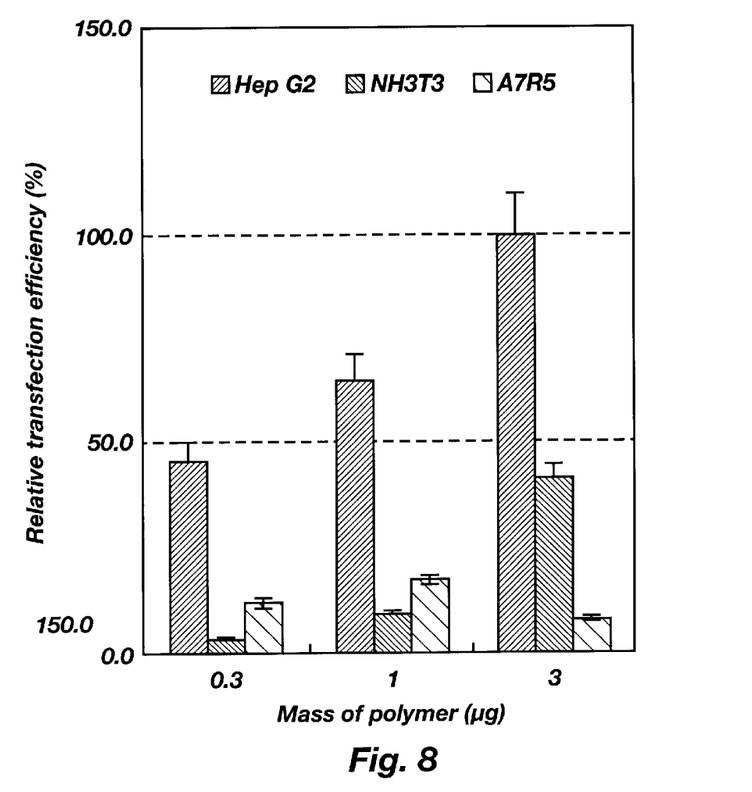
FIG. 8 shows a comparison of transfection efficiency of the composition of the present invention on various cell lines: hatched bars—Hep G2 cells; solid bars—NIH3T3 cells; stippled bars—A7R5 cells.

In this example, Hep G2 cells were transfected with pSV-β-gal/Lac-PEG-PLL according to the procedures of Example 6. Various gene carriers were tested, using a concentration of 3 μg per well of a 96-well plate (30 μg/mL in cell culture medium). The gene carriers were incubated for 4 hours with cells at 37° C., and then cell viability was determined by the method of Y. H. Choi et al, Polyethylene Glyco-grafted Poly-L-lysine as Polymeric Gene Carrier, J. Control. Rel. (1997), hereby incorporated by reference. Cytotoxicity of the synthesized carriers for Hep G2 cells is shown in FIG. 7. Hep G2 cells were incubated in the presence of 30 μg/mL of gene carrier for 4 hours. The 30 μg/mL concentration was chosen because PEG-PLL and Lac-PEG-PLL showed their best transfection efficiency at that concentration. For Lac-PEG-PLL, no cytotoxicity was observed in Hep G2 cells, whereas PLL showed moderate to high cytotoxicity. The difference in lactose-PEG substitution ratio gave no significant change in cell viability. It was further supported by the phase contrast microscopic observation that the incubation of Lac-PEG-PLL with Hep G2 cells did not give any significant influence in cell viability. The incubation of PLL for 4 hours with the cells transformed cell morphology, but PEG-g-PLL or Lac-PEG-PLL at the same concentration and incubation time did not significantly alter the cell morphology.

EXAMPLE 8
Influence of DNA Quantity on Transfection

Figure 9:
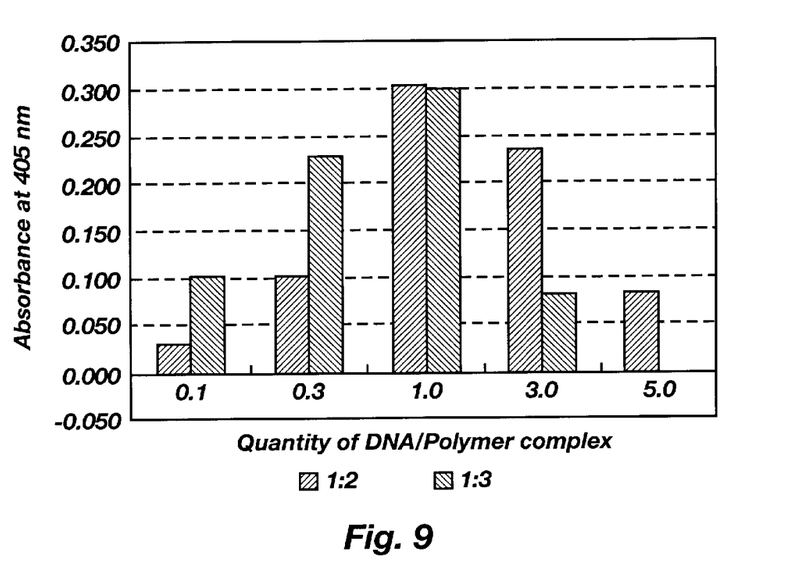
FIG. 9 shows the effect of the quantity of DNA on transfection; hatched bars—DNA:polymer composition is 1:2; solid bars—DNA:polymer composition is 1:3.

The influence of plasmid DNA quantity on transfection was tested. Transfection was carried out according to the procedure of the examples above. 30 mole % Lac-PEG-PLL was used. The amount of pSV-β-gal varied from 0.1 to 5 μg. The weight ratio of DNA to carrier was 1:2 or 1:3. The transfection conditions included 10% FBS and 100 μM chloroquine. After transfection and subsequent culture for 48 hours, the cells were lysed and assayed for βgalactosidase activity. The results shown in FIG. 9 reveal that 1 μg of plasmid DNA gave the best result under these conditions.

EXAMPLE 9
Influence of Time on Transfection

Figure 10:
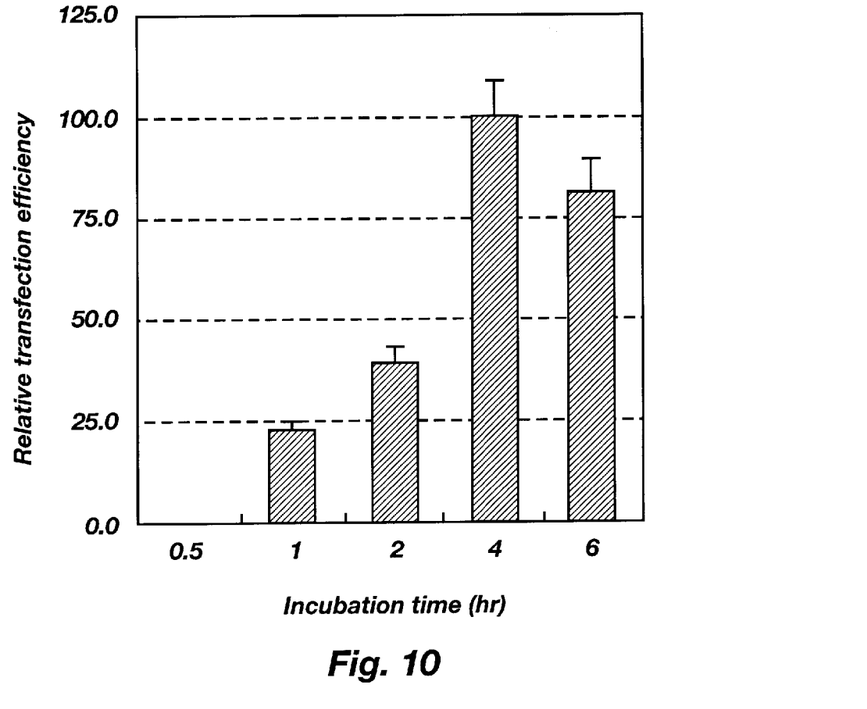
FIG. 10 shows the effect of incubation time on the efficiency of transfection.

The effect of time on transfection was examined. Transfection was carried out according to the procedure described in the examples above. 30 mole % Lac-PEG-PLL was used to transform Hep G2 cells with 1 μg of pSV-β-gal at a 1:3 ratio of plasmid to Lac-PEG-PLL. Transfection time varied from 0.5 to 6 hours in the presence of 10% FBS and 100 μM chloroquine. Following transfection, the cells were incubated for 48 hours and then assayed for β-galactosidase activity. The results shown in FIG. 10 indicate that the best transfection efficiency was obtained with a 4 hour incubation.

EXAMPLE 10
Influence of Time on Gene Expression

Figure 11:
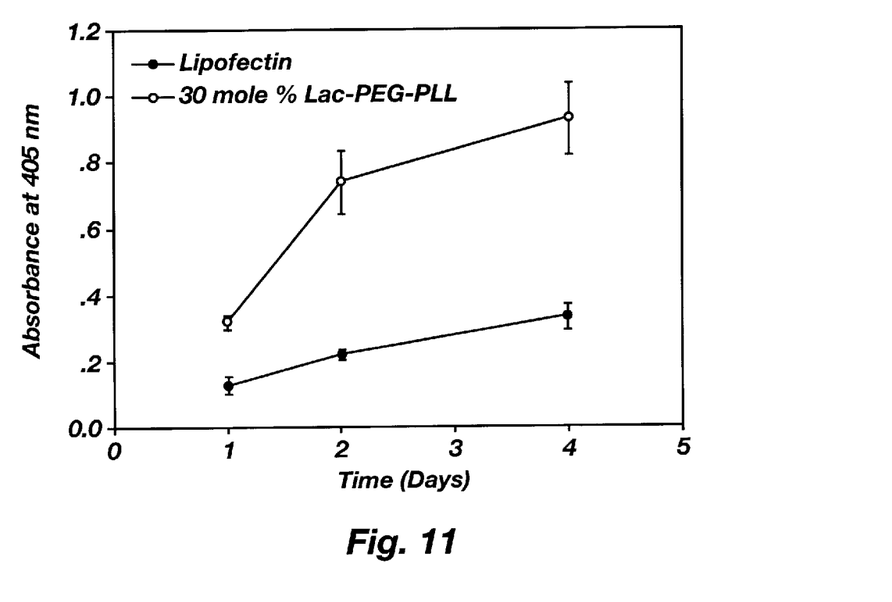
FIG. 11 shows the effects of incubation time on gene expression of transfected cells.

Either LIPOFECTIN reagent or 30 mole % Lac-PEG-PLL was used as a gene carrier. Transfection was carried out according to the procedure of the example above. The amount of pSV-β-gal was 1 μg at a 1:3 ratio of plasmid DNA to carrier. After 4 hours of incubation with Hep G2 cells, the transfection medium was removed and the cells were incubated. At times from 1 to 4 days, the cells were lysed and assayed for β-galactosidase activity. The results shown in FIG. 11 indicate that the presence of Lac-PEG-PLL was much more efficient than that of LIPOFECTIN reagent in mediating transfection under these conditions. For both of the carriers, β-galactosidase activity increased over time. Lac-PEG-PLL, however, gave β-galactosidase activity on day 1 as was obtained with LIPOFECTIN reagent on day 4 of incubation.

The expression was maintained throughout the 96 hours observation period. The maintenance of gene expression up to 96 hours is an advantage of the gene carriers of the present invention for transfection in cultured cells because such stamina of expression provides a window during which manipulation of transfected cells can occur. It is known that the transfected luciferase activity in human macrophage with mannosylated PLL/DNA was maximal after only 24 hours, then rapidly diminished to only 2% after 72 hours.

EXAMPLE 11

Alternative Synthesis Process for Lac-PEG-PLL

Figure 12:
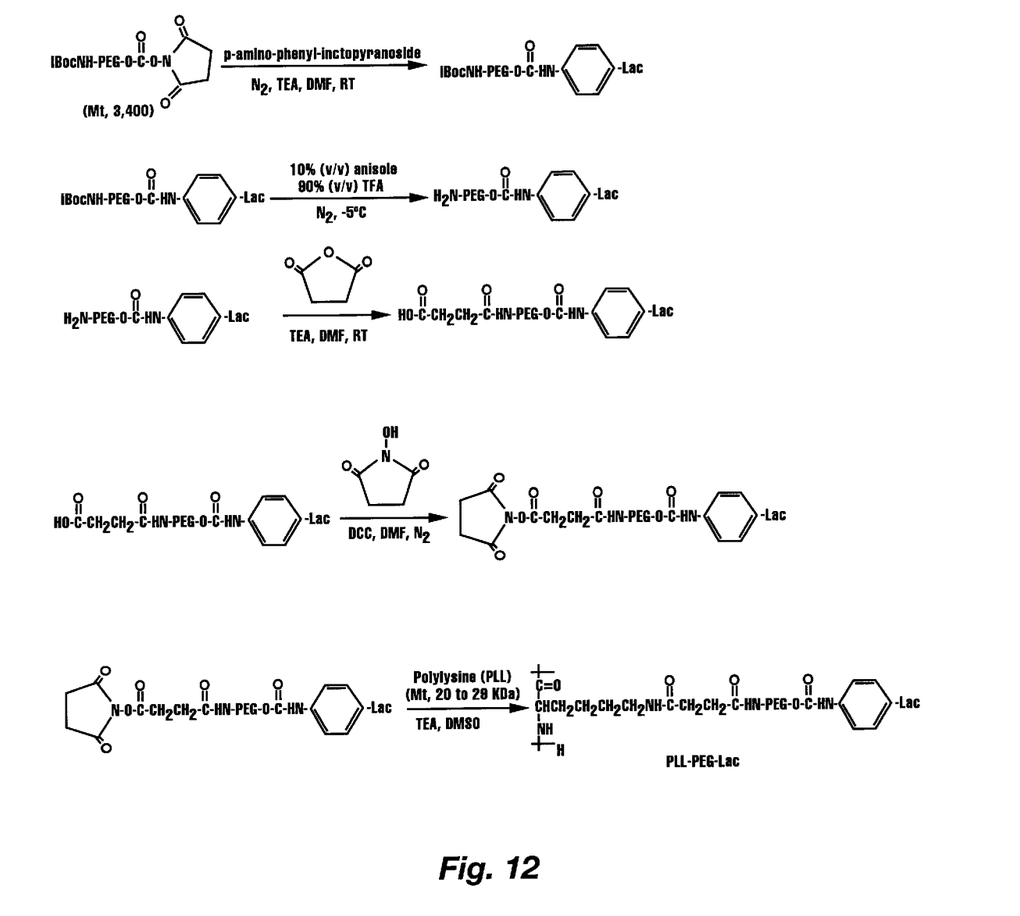
FIG. 12 shows another scheme for synthesis of Lac-PEG-PLL.

An alternative syntheis pathway for Lac-PEG-PLL is illustrated in FIG. 12 and described as following:

1) Synthesis of Lac-PEG diacid with molecular weight of PEG 3,400:

1.08 g of tert-butyl carbonate amine-polyethylene glycol methyl carboxy succinimide (Shearwater Polymer, Inc.) was dissolved in 20 mL of DMF containing 50 mg of TEA and purged with nitrogen. 0.14 g (0.33 micro mole) of p-amino-phenyl-lactopyranoide (PAPL, Sigma) was added and stirred overnight. The DMF, unreached PAPL, hydroxy succinimide and TEA were removed by dialysis against DI water with Spectrum membrane with MWCO of 1,000. The product was obtained by lyophilization.

2) Synthesis of amino-PEG-Lac:

The above-product was dissolved in trifluroacetic acid containing 10% (v/v) of anisole at −5° C. purged with nitrogen and stirred one hour. The product was precipitated with diethyl ether and filtered. The precipitate was washed with ether three times. Finally the product was further purified by dialysis against DI water with Spectrum membrane with MWCO 1,000. The amino-PEG-Lac was obtained by lyophilization.

3) Synthesis of Succinic acid-PEG-Lac:

The amino-PEG-Lac was converted to succinic acid PEG-Lac by reacting amino-PEG-Lac with succinic anhydride (Aldrich) 0.76 g of amino-PEG-Lac was dissolved in 10 ml of toluene containing 22.0 mg of succinic anhydride and reflexed for 6 hours. The polymer Suc-PEG-Lac was then precipitated with excess of ether. The precipitate was washed with ether for three times. Finally the product was dried under vacuum for three days.

0.39 of Suc-PEG-Lac was dissolved in 2 mL of DMF containing 12.7 mg of N-hydroxysuccinimide. Then 22.7 mg of DDC and 15 mg of TEA were added, and stirred overnight. The precipitate was removed by filtration. The product HOSu-Suc-PEG-Lac was completely dried under vacuum for 2 days.

4) Synthesis of Lac-PEG-PLL:

As an example, the synthesis of Lac-PEG-PPL with 5% of Lac-PEG was described 23.7 mg (0.11 micro mole) of Suc-PEG-Lac dissolved in 0.5 mL of DMSO was added drop by drop to a 2 mL of DMSO containing 25 mg (0.11 micro mole) of PLL in 5 minutes and stirred for an additional 5 hours. The product was then dialyzed against DI water to remove the DMSO, N-hydroxy succinimide and unreached PEG by using Spectrum membrane with MWCO 25,000 for 2 days. The final product was obtained by lyophilization and stored at −20° C.

EXAMPLE 12

Synthesis Process for Gal-PEG-PLL

Figure 13:
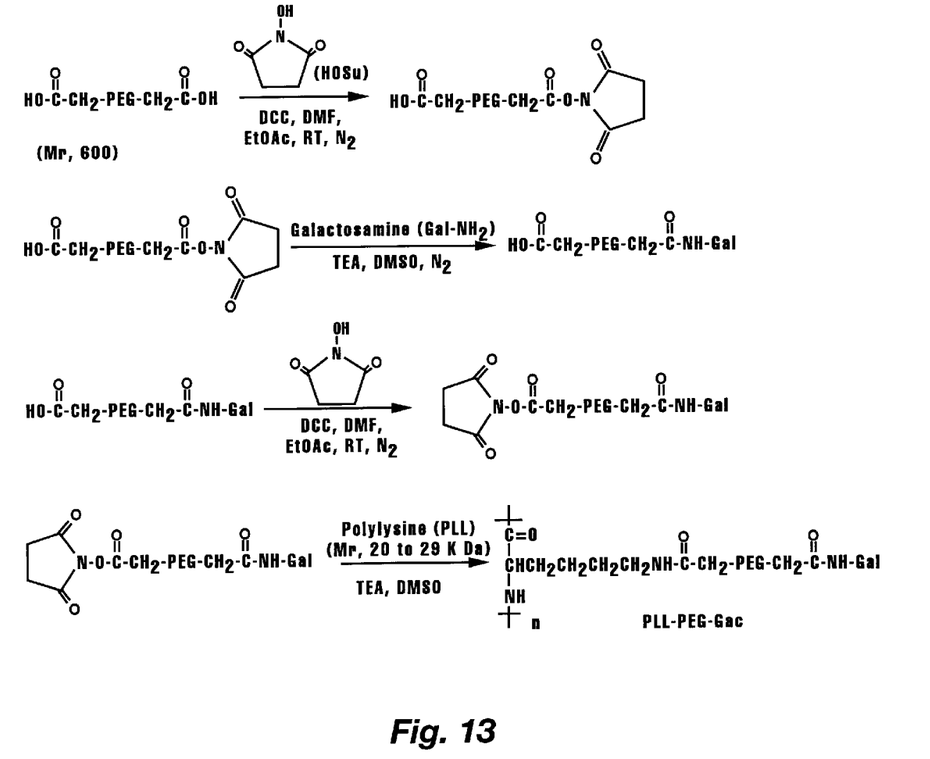
FIG. 13 shows the scheme for synthesis of Gal-PEG-PLL.

An alternative syntheis pathway for Lac-PEG-PLL is illustrated in FIG. 13 and described as following:

1) Synthesis of HOSu-PEG diacid:

1.20 g (2.0 micro mole) of PEG diacid (mol. Wt., 600, Fluka, Ronkonloma, N.Y.) was dissolved in 20 ml of ethyl acetate (Aldrich) at room temperature. Then 69.0 mg (0.6 micro mole) of N-hydroxysuccinimide (Aldrich) and 144.4 mg (0.70 micro mole) of N,N'-dicyclohexylcarbonimide (Aldrich) and 300 µL were added. The above solution was stirred over night at room temperature. After the reaction, the precipitate dicycohexylurea was removed via filtration using Durapore filter membrane with pore size of 0.22 µm, and washed three times with ethyl acetate. The ethyl acetate was removed by Rotavap under vacuum. The residue was dissolved in methylene bichloride and then the PEG product was precipitated with diethyl ether at −20° C. The precipitate was collected by centrifugation at −20° C. and decanting the supernatant. Finally the HOSu-PEG diacid was completely dried at room temperature under vacuum in several days.

2) Synthesis of Gal-PEG:

350 mg (0.5 micro mole) of HOSu-PEG diacid, 107.8 mg (0.5 micro mole) of D(+)-galactosamine (Sigma), 101 mg (1.0 micro mole) of triethylamin (TEA, Aldrich) were dissolved in 2 ml of Dimethyl sulfoxide (DMSO, Adrich) at room temperature and stirred overnight. The unreached galactosamin, DMSO, TEA and N-hydroxysuccinimide were removed by precipitating the PEG derivatives at −70° C. and the precipitate was obtained by centrifugation. The PEG diacid produced by hydrolysis of HOSu-PEG was removed by ion exchange column. The Galactose-PEG (Gal-PEG) was further purified against DI water and obtained by lyophilization.

3) Grafting of Gal-PEG diacid to PLL:

A similar grafting process of Lac-PEG-PPL as described in Example 2 was used to graft Gal-PEG diacid to PLL.

The above Examples are presented for illustrative purposes only and are not intended, and should not be construed to limit the invention in any manner. Various modifications of the compounds and methods of the invention may be made without departing from the spirit or scope thereof and it is to be understood that the invention is intended to be limited only as defined in the appended claims.

What is claimed is:

1. A polymeric compound for gene delivery comprising a polyethylene glycol(PEG) grafted poly(L-lysine)(PLL) and a targeting moiety capable of targeting to a hepatocyte cell, wherein at least one free amino function of said PLL is covalently conjugated with said PEG which in turn is covalently conjugated with said targeting moiety, and the grafted PLL contains at least 50% unsubstituted free amino functional groups.

2. The compound of claim 1 wherein said PEG has a molecular weight between 0.5 to 20K daltons.

3. The compound of claim 2 wherein said PEG has a molecular weight between 0.5 to 5K daltons.

4. The compound of claim 3 wherein said PLL contains at 60 to 97% unsubstituted free amino function groups.

5. The compound of claim 4 wherein said PLL has a molecular weight between 2K to 100K daltons.

6. The compound of claim 5 wherein said PLL has a molecular weight between 20K to 30K daltons.

7. The compound of claim 1 wherein the targeting moiety is recognizable by a cell membrane receptor and is selected from the group consisting of lactose and galactose.

8. The compound of claim 1 wherein said TM is lactose.

9. The compound of claim 1 wherein said TM is galactose.

10. A composition comprising the compound of claim 1 and a nucleic acid.

11. The composition of claim 10 wherein the nucleic acid comprising a DNA sequence encodes a genetic marker selected from the group consisting of luciferase gene, β-galactosidase gene, hygromycin resistance, neomycin resistance, and chloramphenicol acetyl transferase.

12. The composition of claim 10 wherein the nucleic acid comprising a DNA sequence encodes a protein selected from the group consisting of low density lipoprotein receptors, coagulation factors, gene suppressors of tumors, major histocompatibility proteins, antioncogenes, p16, p53, thymidine kinase, IL2, IL 4, and TNFa.

13. The composition of claim 10 wherein the nucleic acid comprising a DNA sequence encodes a viral antigen.

14. The composition of claim 10 wherein the nucleic acid encodes an RNA selected from the group consisting of a sense RNA, an antisense RNA, and a ribozyme.

15. The composition of claim 10 wherein the nucleic acid encodes a lectin, a mannose receptor, a sialoadhesin, or a retroviral transactiviating factor.

16. A method of transfecting cells in vitro comprising contacting said cells with the composition of claim 10 under conditions wherein said composition enters said cells, and the nucleic acid of said composition is released.

17. A method of transfecting cells in vitro bearing a receptor recognizing a targeting moiety comprising contacting said cells with the composition comprising a compound of claim 1 and a nucleic acid, under conditions wherein said composition enters said cells, and the nucleic acid of said composition is released.

18. The method according to claim 17 wherein the targeting moiety is a galactose containing saccharide selected from a group consisting of lactose and galactose.

19. The method according to claim 18 wherein said targeting moiety is lactose.

20. The method according to claim 19 wherein said targeting moiety is galactose.

21. The method according to claim 20 wherein the cells are hepatocyte cells.

22. The method according to claim 20 wherein the cells are hepatoma cells.

* * * * *